United States Patent [19]

Kaufhold

[11] Patent Number: 4,772,758

[45] Date of Patent: Sep. 20, 1988

[54] PROCESS FOR THE PRODUCTION OF TECHNICALLY PURE, CHLORINE-FREE CYCLOHEXADECADIENE

[75] Inventor: Manfred Kaufhold, Marl, Fed. Rep. of Germany

[73] Assignee: Huels Aktiengesellschaft, Marl, Fed. Rep. of Germany

[21] Appl. No.: 37,891

[22] Filed: Apr. 13, 1987

[30] Foreign Application Priority Data

Apr. 14, 1986 [DE] Fed. Rep. of Germany ....... 3612539

[51] Int. Cl.⁴ .................. C10G 19/02; C07C 7/00; C07C 7/148
[52] U.S. Cl. .................................. 585/803; 585/853; 208/262.1
[58] Field of Search ............... 585/803, 853; 208/262, 208/180, 183

[56] References Cited

U.S. PATENT DOCUMENTS 4,097,369 6/1978 Ebel et al. ............................ 208/180
4,327,027 4/1982 Howard et al. ................... 260/340.3

Primary Examiner—Patrick P. Garvin
Assistant Examiner—George R. Fourson
Attorney, Agent, or Firm—Millen & White

[57] ABSTRACT

A process for producing technically pure, chlorine-free cyclohexadecadiene by purifying the product mixture obtained preferably from the metathesis of cyclooctene by first removing by distillation the low boiling $C_6$ hydrocarbons and any water that may be present, then treating the sump product with a solution of a strongly alkaline compound at about 100°–250° C. After separation of the thus-formed salts, the thus-pretreated product mixture may be subjected to fractional distillation in the usual way.

21 Claims, No Drawings

PROCESS FOR THE PRODUCTION OF TECHNICALLY PURE, CHLORINE-FREE CYCLOHEXADECADIENE

BACKGROUND OF THE INVENTION

The invention relates to a process for the production of technically pure, chlorine-free cyclohexadecadiene, technically pure meaning a cyclohexadecadiene content, according to analysis by gas chromatography, of around 90% or higher; and chlorine-free meaning a chlorine content smaller than 10 ppm. Products of this quality are suitable for further industrial processing. Cyclohexadecadiene having such a purity is a valuable starting material, for example, for the conventional musk fragrance compounds cyclohexadecanone, cyclohexadecenone, and cyclohexadecanolide, and others. The cyclohexadecadiene utilized in the purification is preferably obtained in the metathesis of cyclooctene, for example with a $WCl_6$ containing catalyst as describes in the DE-OS No. 17 93 138, example 1 (=U.S. Pat. No. 3,439,056, example 1 and U.S. Pat. No. 3,935,270).

Suggestions for the syntheses of musk fragrances based on cyclohexadecadiene have been advanced in the literature. Thus, Lawson G. Wideman (in *Journal of Org. Chem.* 33 No. 12:4541 [1968]) describes the monoaddition of boron hydride to cyclohexadecadiene and oxidation of the adduct to the unsaturated ketone. The production and reaction of boron hydride is costly industrially and very expensive from the viewpoint of consumption of chemicals; in other words, this reaction is not feasible for industrial realization for economic reasons.

In a synthesis proposed by B. D. Mookherjee et al., the monoepoxide of cyclohexadecadiene is first prepared and then converted with butyllithium into the corresponding, unsaturated alcohol. Other, less costly chemicals are unsuitable for this reaction. The subsequent reaction of the unsaturated ketone with methylmagnesium bromide and the subsequent hydrogenation yields muscone (see *J. Org. Chem.* 36 No. 22:3266 [1971]). Industrial realization of this synthesis method is likewise very complicated, and the chemicals required are costly.

A process is desirable wherein the crude cyclohexadecadiene—preferably stemming from the industrial metathesis of cyclooctene—could be employed and used to produce therefrom, by catalytic reactions, cyclohexadecanone, for example. In this method, the diene would have to be hydrogenated catalytically to the cyclohexadecane and the latter would have to be oxidized with air to the ketone; alternatively, the monoepoxide of cyclohexadecadiene could be catalytically hydrogenated to the saturated epoxide which is then isomerized catalytically to the ketone.

The problem residing in these reaction sequences is the low purity of the crude cyclohexadecadiene, especially its relatively high chlorine content of 200–500 ppm. Chlorine-containing products cannot be processed in the usual industrial installations on account of resultant corrosion.

In hydrogenation with a cyclohexadecadiene of high chlorine content, the catalyst is damaged, its activity is reduced, and its lifetime is shortened.

In contrast thereto, the aforementioned expensive reactions—published in the literature—with the chlorine-containing diene can be performed without any problems.

Therefore, great interest exists in catalytic processes than can be performed industrially in a simple fashion, for the preparation of musk fragrances based on cyclohexadecadiene, inasmuch as musk fragrance is a very universally desired scent note and is usually considered to be the animalistic note of perfumes (DOS No. 2,111,753).

SUMMARY OF THE INVENTION

Therefore, it is an object of this invention to provide a process for the purification and dechlorination of crude, industrially obtained cyclohexadecadiene by inexpensive chemicals.

Upon further study of the specification and appended claims, further objects and advantages of this invention will become apparent to those skilled in the art.

The objects have been attained by the provision of a technically pure, chlorine-free cyclohexadecadiene, i.e., one having a chlorine content smaller than 10 ppm and being, according to GC analysis, of over 90% strength, by the following purification process:

1. Removing the low-boiling compounds and, where present, water from cyclohexadecadiene obtained, e.g., from the metathesis of cyclooctene.

2. Adding a strongly alkaline compound, e.g., a solution of an alkali metal alcoholate in the corresponding alcohol, and agitating at elevated temperature wherein any solvent, such as the added alcohol, for example, may be removed by distillation.

3. Cooling, the mixture so as to form a salt, separating the thus-formed salt, for example by washing with water, and separating the organic phase.

4. Isolating the desired compounds, e.g., fractionally distilling the oil layer, to obtain $C_8$, $C_{16}$ and $C_{24}$ compounds.

The invention also relates to the combination per se of 2 and 3.

($C_8$ compounds refer to substances whose empirical formulae have 8 carbon atoms, etc.)

It has now been found surprisingly that, after the reaction with the strongly alkaline compound, a chlorine content of, e.g., 200–500 ppm can be lowered to, e.g., 50–100 ppm and further these chlorine-containing reaction products could be processed without danger of corrosion in apparatuses made of the usual materials. After fractional distillation, the valuable distillation cuts that contain $C_8$ and $C_{16}$ compounds are free of chlorine whereas the useless distillation foreruns and intermediate runs contain the residual chlorine.

This surprising finding thus makes it possible to obtain technically pure, chlorine-free cyclohexadecadiene in a simple way.

DETAILED DISCUSSION

In order to facilitate a description of the preferred manner of performing the individual stages, the following composition of a suitable starting material is set forth, namely a cyclohexadecadiene stemming from the metathesis of cyclooctene. This composition is to be considered merely as a non-limiting example. The preferred reaction conditions detailed below are equally applicable to all starting material compositions of the invention.

| | |
|---|---|
| $C_6$ Hydrocarbons | about 20% |

-continued

| | |
|---|---|
| Toluene | about 5% |
| Cyclooctene | about 1% |
| Cyclooctane | about 20% |
| $C_{16}$ Hydrocarbons | about 30% |
| $C_{24}$ Hydrocarbons | about 5% |
| Unidentified compounds | about 19% |
| | about 100% |

The chlorine content is 240 ppm.

Preferably, the process of this invention takes place in the following stages:

1. Removing, by distillation, $C_6$ hydrocarbons and suspended and dissolved water under normal pressure up to a sump temperature of about 100°–170° C., preferably about 140°–150° C.

2. Adding a strongly alkaline compound, e.g., one having a pKb of $>10^{-3}$, preferably $>10^{-2}$, for example an alkali metal alcoholate solution in the corresponding alcohol, under agitation and preferably with removal of the solvent alcohol by distillation. Preferred alkali metal alcoholates are sodium and potassium alcoholates. Preferably, the methylates, ethylates, n-, iso- or tert-butylates are utilized. The alkali metal alcoholate is preferably added, in amounts of about 1–100 moles per 1 gram atom of chlorine, preferably 5–50 moles per 1 gram atom of chlorine, with respect to the chlorine content of the starting material. Treatment with the alkali metal alcoholate takes place generally at temperatures of about 100°–250° C., preferably about 120°–170° C., more preferably about 140°–150° C. Other strongly alkaline compounds would be equally suitable. Examples of such compounds include Natriumamide, Natriumhydride and analogous complexis compounds. However alkaline- or alkaline-earth metal hydroxides ar unsuitable.

Typically, the resultant content of $C_6$ or smaller compounds is thus lowered to values less than 1000 ppm and $H_2O$ contents to less than 100 ppm.

3. Cooling to form a salt, e.g., to 50°–0° C., preferably to room temperature, and removing the thus-formed salts and optionally the excess alcoholate, for example by a water washing step. The water washing step is generally performed at temperatures of 10°–50° C. Preferably, 10–100 wt % of water, based on the starting material, is added in the water washing step.

The chlorine content after the washing step is 50–100 ppm.

4. Conventionally, fractionally distilling the resultant solution, thereby obtaining chlorine-free $C_8$, $C_{16}$, etc., distillation cuts. Although fractional distillation is the preferred method of separating desired products, it is contemplated that the process of the invention may advantageously be employed with other conventional isolation techniques where desirable.

The first stage is preferably carried out in glass or enameled apparatuses, and the 2nd to 4th stages are preferably conducted in the conventional steel installations, without there being any danger of corrosion.

As mentioned above, the thus-obtained, technically pure, chlorine-free cyclohexadecadiene can be utilized for the conventional catalytic hydrogenation or for epoxidation in order to arrive at valuable, inexpensive starting compounds for the production of musk fragrance compounds.

Additional numerical data can be derived from the examples set forth below which are to explain the process of this invention in greater detail. Of course, other conditions equivalent to those mentioned above are fully encompassed within the scope of this invention, e.g., temperature/pressure conditions for the distillation, etc.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, all temperatures are set forth uncorrected in degrees Celsius; unless otherwise indicated, all parts and percentages are by weight.

EXAMPLE 1

A product is used from the metathesis of cyclooctene having the following composition:

| | |
|---|---|
| $C_6$ Hydrocarbons | 22.3% |
| Toluene | 3.5% |
| Cyclooctene | 0.8% |
| Cyclooctane | 19.3% |
| $C_{16}$ Hydrocarbons | 33.1% |
| $C_{24}$ Hydrocarbons | 4.4% |
| Unidentified compounds | 16.6% |
| | 100.0% |

1,000 g of this product mixture is initially distilled under normal pressure on a glass column having a length of 0.5 m and filled with multifil packing elements, with a ratio of reflux to discharge like 5:1, the sump temperature being raised from $\psi°$ to 149° C. and temperatures of 62°–76° C. being obtained at the head.

The yield is 209 g of distillate which is discarded. The distillation residue shows the following composition:

| | |
|---|---|
| $C_6$ Hydrocarbons | 0.9% |
| Toluene | 4.8% |
| Cyclooctene | 1.0% |
| Cyclooctane | 24.5% |
| $C_{16}$ Hydrocarbons | 42.1% |
| $C_{24}$ Hydrocarbons | 5.6% |
| Unidentified compounds | 21.1% |
| | 100.0% |

The chlorine content lies at 400 ppm.

For dechlorination, a glass apparatus is used consisting of three-necked flask, agitator, thermometer, and distillation device.

500 g of the distillation residue is utilized, and heated under agitation and reflux to boiling, thus obtaining a temperature of 147° C. Then, 12 g of a 30.7% strength sodium methylate-methanol solution is added dropwise within 45 minutes, and the temperature is maintained at about 150° C. In this step, methanol is removed by distillation; this methanol is discarded.

After five hours, the mixture is cooled to room temperature and washed with 300 g of water. Thereafter, the chlorine content is 66 ppm. A glass column having a length of 0.5 m and filled with multifil packing elements is used for the fractional distillation of 500 g of the product treated in this way. The chlorine contents of the resultant fractions are listed in the right-hand column:

| Fr. No. | Temp. °C. (at the Head) | Weight g | Pressure mbar | Ratio Reflux to Discharge | Chlorine Content in ppm |
| --- | --- | --- | --- | --- | --- |
| 1 | 47–83 | 110.2 | 133 | 5:1 | 110 |
| 2 | 83–85 | 98.3 | 133 | 5:1 | 4.5 |
| 3 | 57–158 | 85.2 | 13 | 5:1 | 1000 |
| 4 | 158–163 | 175.2 | 13 | 5:1 | 8 |
| 5 | 163–202 | 8.0 | 13 | 5:1 | 280 |
| Residue | | 20.1 | | | |

Fraction 2, according to analysis by gas chromatography, consists of 3.9% cyclooctene and 94.6% cyclooctane with a chlorine content of merely 4.5 ppm.

Analysis by gas chromatography of a hydrogenated sample from fraction 4 shows a content of cyclohexadecane of 97.4%, i.e. fraction 4 consists of about 97% cyclohexadecadienes. The various isomers cannot be classified by gas chromatography. The low chlorine content, being 8 ppm, permits industrial further processing, such as, for example, catalytic hydrogenation in the ususal way.

The corrosion test is conducted with the product from which the $C_6$ hydrocarbons have been removed by distillation, in such a way that treatment with sodium methylate is carried out in the presence of clamping clips having a weld seam of austenitic CrNiMo steel 1.4571. After a testing period of 256 hours, the test specimens show no corrosion ablation and no corrosion attack.

Analogously, corrosion is tested for during the distillation. After a distillation period of 598 hours, the clamping clip samples of material 1.4571 show no corrosion attack and no corrosion ablation.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of purified, substantially chlorine-free cyclohexadecadiene by purifying a product mixture containing cyclohexadecadiene and chloride-containing products, comprising removing, by distillation, any low-boiling $C_6$ hydrocarbons, as well as any dissolved or suspended water that may be present; then treating the resulting sump product with a strongly alkaline compound at elevated temperature; subsequently cooling until salt-formation occurs; separating of the thus-formed salts and then isolating cyclohexadecadiene by fractional distillation.

2. A process according to claim 1, wherein the strongly alkaline compound is an alkali metal alcoholate.

3. A process according to claim 2, wherein the alkali metal alcoholate is a sodium or potassium alcoholate.

4. A process according to claim 2, wherein the alkali metal alcoholate is used as a solution of alkali metal alcoholate in the corresponding alcohol.

5. A process according to claim 1, wherein the treatment with the strongly alkaline compound is performed at a temperature of about 100°–250° C.

6. A process according to claim 1, wherein the treatment with the strongly alkaline compound is performed at 120°–170° C.

7. A process according to claim 1, wherein the treatment with the strongly alkaline compound is performed at 140°–150° C.

8. A process according to claim 1, wherein the strongly alkaline compound has a $K_B > 10^{-3}$.

9. A process according to claim 2, wherein the alkali metal alcoholate is used in an amount of 1–100 moles per 1 gram-atom of chlorine with respect to the chlorine content of the starting material.

10. A process according to claim 2, wherein the alkali metal alcoholate is used in an amount of 5–50 moles per 1 gram-atom of chlorine, with respect to the chlorine content of the starting material.

11. A process according to claim 6, wherein after treatment with the strongly alkaline compound the sump product is cooled to about 0°–50° C.

12. A process according to claim 6, wherein the salt formed in the treatment with the strongly alkaline compound is removed by a water washing step.

13. A process according to claim 12, wherein during the water washing step, 10–100% by weight of water, based on the starting material, is added.

14. A process according to claim 12, wherein the water washing step is conducted at a temperature of about 10°–50° C.

15. In a process for the production of a purified, substantially chlorine-free cyclohexadecadiene, the improvement comprising reacting a crude cyclohexadecadiene with a strongly alkaline compound at elevated temperature and cooling the resultant product until salt-formation occurs.

16. A process of removing chlorine from a mixture of cyclohexadecadiene and chloride-containing products comprising treating said mixture with a strongly alkaline compound at an elevated temperature of 120°–170° C. and cooling the resultant product to effect salt formation.

17. A process of claim 16, further comprising prior to said treating step, distilling said mixture to remove therefrom contained low-boiling $C_6$ hydrocarbons, water or both.

18. A process of claim 17, further comprising after said cooling step, separating the salts from said mixture and then isolating cyclohexadecadiene by fractional distillation.

19. A process according to claim 1, wherein the cyclohexadecadiene present in the produce mixture purified is obtained from the metathesis of cyclooctene.

20. A process according to claim 1, wherein the product mixture purified has the following composition in % by weight:

| | |
| --- | --- |
| $C_6$ Hydrocarbons | about 20% |
| Toluene | about 5% |
| Cyclooctene | about 1% |
| Cyclooctane | about 20% |
| $C_{16}$ Hydrocarbons | about 30% |
| $C_{24}$ Hydrocarbons | about 5% |
| unidentified compounds | about 19% |

21. A process according to claim 1, wherein the chlorine content of the purified cyclohexadecadiene is 100 ppm or less.

* * * * *